United States Patent
Kwon et al.

(10) Patent No.: US 9,051,262 B2
(45) Date of Patent: Jun. 9, 2015

(54) PLASTICIZER AND METHOD OF PREPARING THE SAME

(75) Inventors: Tae Wook Kwon, Daejeon (KR); Sung Gi Lee, Daejeon (KR); Ki Nam Chung, Daejeon (KR); Seung Gweon Hong, Daejeon (KR)

(73) Assignees: SK INNOVATION CO., LTD., Seoul (KR); SK GLOBAL CHEMICAL CO., LTD., Seoul (KR)

( * ) Notice: Subject to any disclaimer, the term of this patent is extended or adjusted under 35 U.S.C. 154(b) by 72 days.

(21) Appl. No.: 13/695,736

(22) PCT Filed: Feb. 28, 2011

(86) PCT No.: PCT/KR2011/001392
§ 371 (c)(1),
(2), (4) Date: Nov. 9, 2012

(87) PCT Pub. No.: WO2011/139016
PCT Pub. Date: Nov. 10, 2011

(65) Prior Publication Data
US 2013/0072611 A1    Mar. 21, 2013

(30) Foreign Application Priority Data
May 4, 2010    (KR) .................. 10-2010-0042145

(51) Int. Cl.
| | |
|---|---|
| *C08K 5/00* | (2006.01) |
| *C08K 5/09* | (2006.01) |
| *C09D 11/06* | (2006.01) |
| *C07C 69/78* | (2006.01) |
| *C08K 5/103* | (2006.01) |
| *C08K 5/101* | (2006.01) |

(52) U.S. Cl.
CPC ............. *C07C 69/78* (2013.01); *C08K 5/103* (2013.01); *C08K 5/101* (2013.01)

(58) Field of Classification Search
None
See application file for complete search history.

(56) References Cited

U.S. PATENT DOCUMENTS

| | | | |
|---|---|---|---|
| 6,652,774 B2 * | 11/2003 | Zhou et al. | ............... 252/182.24 |
| 2006/0229394 A1 | 10/2006 | Kim et al. | |
| 2009/0149585 A1 | 6/2009 | De Quadros et al. | |
| 2010/0093885 A1 | 4/2010 | Hansel et al. | |
| 2011/0166271 A1 * | 7/2011 | Hong et al. | ................... 524/287 |

FOREIGN PATENT DOCUMENTS

| | | | |
|---|---|---|---|
| JP | 11-349766 | * | 12/1999 |
| JP | H11349765 A | | 12/1999 |
| JP | H11349766 A | | 12/1999 |
| JP | 2007-504126 A | | 3/2007 |
| JP | 2008-534734 A | | 8/2008 |
| KR | 10-2008-0114278 A | | 12/2008 |
| KR | 10-2009-0009437 A | | 1/2009 |
| KR | 10-2010-0031391 A | | 3/2010 |
| WO | WO 2010/030096 A2 | * | 3/2010 |

OTHER PUBLICATIONS

Machine Translation of JP-11-349766, Plasticizer for Vinyl Chloride-Based Resin, pp. 1-12.*
Full English Translation of Sugita et al. JP 11-349766, Dec. 1999, pp. 1-28.*
PCT/KR2011/001392, International Search Report dated Nov. 21, 2011, 4 pages.

* cited by examiner

*Primary Examiner* — Susannah Chung
*Assistant Examiner* — Robert T Butcher
(74) *Attorney, Agent, or Firm* — Abelman, Frayne & Schwab

(57) ABSTRACT

The present invention provides an ester plasticizer for polyvinyl chloride (PVC) resin, epoxy resin or urethane resin and a method of preparing the same. More particularly, the present invention provides an ester plasticizer using triacetin and coconut oil-based biodiesel as raw materials, which can prepare a resin composition having excellent plasticizing efficiency and improved physical properties such as tensile strength and the like.

When a polyvinyl chloride resin or the like is manufactured using the ester plasticizer, there are advantages in that an environment-friendly product having an excellent plasticizing efficiency and in that the physical properties such as hardness, tensile strength, etc. of the product are improved.

12 Claims, No Drawings

PLASTICIZER AND METHOD OF PREPARING THE SAME

RELATED APPLICATIONS

This application is a United Sates national phase application under 35 USC §371of PCT/KR2011/001392 filed on Feb. 28, 2011, and claims the benefit under 35 USC §119 of Korean patent application number KR 10-2010-0042145 filed May 4, 2010, the disclosure of which are incorporated herein by reference in their entireties.

TECHNICAL FIELD

The present invention relates to an ester plasticizer for polyvinyl chloride (PVC) resin, epoxy resin or urethane resin and a method of preparing the same. More particularly, the present invention relates to an ester plasticizer using triacetin and coconut oil-based biodiesel as raw materials, which can prepare a resin composition having an excellent plasticizing efficiency and improved physical properties such as tensile strength and the like.

BACKGROUND ART

Various physical properties can be provided to a resin composition such as a polyvinyl chloride resin composition, a urethane resin composition, an epoxy resin composition or the like, by suitably adding various additives such as a plasticizer, a stabilizer, filler, pigment and the like.

Among such additives, a plasticizer is an essential additive providing various physical properties and functions, such as processability, flexibility, electrical insulation, adhesivity and the like, to a resin. Low volatility, as a very important factor of a plasticizer, is important both when a plasticizer is mixed in a plastic composition and when a shaped product containing a plasticizer is practically used. Further, plasticizers used in the field of foods, drinks, medicals and medicines must be harmless to the health However, it is predicted that the usage of a phthalate plasticizer, which has been widely used as a plasticizer, will be remarkably reduced in the future because of the toxicity issues about reproducibility in the laws regulating toxic materials. Therefore, it is required to develop a plasticizer including an ester whose basic structure contains no phthalate and which has a plasticizing efficiency equal to that of a phthalate plasticizer.

DISCLOSURE

Technical Problem

In order to solve the above-mentioned problem, the present inventors carefully examined ester compounds as a plasticizer for resins such as polyvinyl chloride etc. As a result, they found that a specifically-structured novel ester compound obtained by the transesterification reaction of triacetin, coconut oil-based biodiesel and methyl benzoate can be used as a plasticizer, and, particularly, is excellent as a plasticizer for a polyvinyl chloride resin. Based on these findings, the present invention was completed. Accordingly, the present invention intends to provide a novel environment-friendly ester plasticizer having physical properties equal to or superior to conventional phthalate plasticizers, and a method of preparing the same.

Technical Solution

In order to accomplish the above object, a first aspect of the present invention provides a plasticizer composition, including: glycerin triester represented by General Formula $CH_2(OR_1)CH(OR_2)CH_2(OR_3)$, wherein one or two of $R_1$ to $R_3$ is an acetyl group, and the other one or two is a compound selected from the group consisting of an acyl group of 6 to 13 carbon atoms and a benzoyl group, and the compound is included in an amount of 80 wt % or more based on a total amount of the plasticizer composition.

A second aspect of the present invention provides a method of preparing a plasticizer composition, comprising: fractionating coconut oil methyl ester to obtain a fatty acid methyl ester of C6~C12; mixing the fatty acid methyl ester with triacetin and methyl benzoate; and transesterifying the mixture using a basic catalyst.

Advantageous Effects

When a polyvinyl chloride resin or the like is manufactured using the ester plasticizer of the present invention, there are advantages in that an excellent product can be obtained in terms of plasticizing efficiency, in that the physical properties such as tensile strength and the like of the product are improved, and in that the product can be obtained using the ester plasticizer which is environment-friendly compared to conventional phthalate plasticizers.

BEST MODE

The objects, features and advantages of the present invention will be more clearly understood from the following detailed description, and thus those skilled in the art can easily carry out the technical idea of the present invention. Further, in the description of the present invention, when it is determined that the detailed description of the related art would obscure the gist of the present invention, the description thereof will be omitted.

Hereinafter, the present invention will be described in detail.

The plasticizer composition according to the present invention includes ester compounds different from each other, and, particularly, includes: glycerin triester represented by General Formula $CH_2(OR_1)CH(OR_2)CH_2(OR_3)$, wherein one or two of R1 to R3 is an acetyl group, and the other one or two is a triester compound selected from the group consisting of an acyl group of 6 to 13 carbon atoms and a benzoyl group, and the triester compound is included in an amount of 80 wt % or more based on a total amount of the plasticizer composition Particularly, the plasticizer composition is a mixture of six triester compounds, and, more particularly, is a mixture of compounds having Structural Formulae (1) to (9) below:

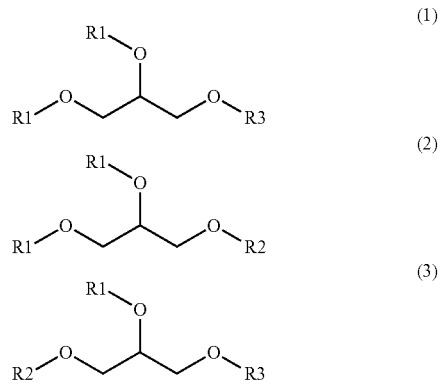

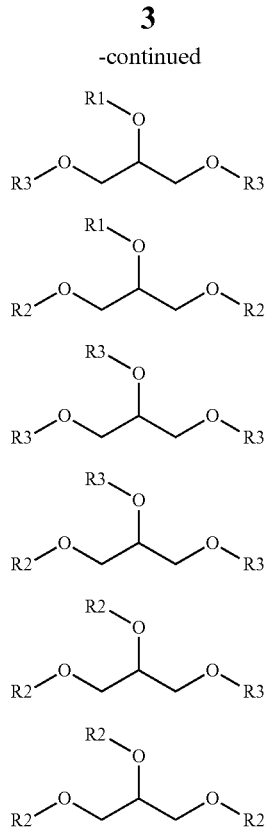

wherein R1 is an acetyl group, R2 is an acyl group of 6 to 21 carbon atoms, R3 is a benzoyl group, and the positions of R1, R2 and R3 in the same compound may be changed.

The triester compounds, each having General Formula $CH_2(OR_1)CH(OR_2)CH_2(OR_3)$, wherein one or two of R1 to R3 is an acetyl group, and the other one or two is selected from the group consisting of an acyl group of 6 to 13 carbon atoms and a benzoyl group, correspond to compounds of Structural Formulae (1) to (5) of the compounds of Structural Formulae (1) to (9).

Each of the triesters of Structural Formulae (1) and (2) has a structure in which one benzoyl group or one acyl group of 6 to 21 carbon atoms is disposed at the ester end thereof (referred to as a "mono-functional triester"), each of the triesters of Structural Formulae (3) to (5) has a structure in which two benzoyl groups or two acyl groups of 6 to 21 carbon atoms are disposed at the ester end thereof (referred to as a "di-functional triester"), and each of the triesters of Structural Formulae (6) to (9) has a structure in which three benzoyl groups or three acyl groups of 6 to 21 carbon atoms are disposed at the ester end thereof (referred to as a "tri-functional triester") The plasticizer composition according to the present invention is a mixture of the nine kinds of triester compounds. Preferably, the amount of the mono-functional triester may be 40~80 wt %, the amount of the di-functional triester may be 20~60 wt %, and the amount of the three-functional triester may be 0~20 wt %, based on the total amount of the plasticizer composition. More preferably, the amount of the mono-functional triester may be 40~75 wt %, the amount of the di-functional triester may be 30~50 wt %, and the amount of the three-functional triester may be 2~20 wt %, based on the total amount of the plasticizer composition. According to the composition ratio above, the plasticizer composition of the present invention includes 15~40 wt % of aromatic components.

In the present invention, when the amount of the mono-functional triester is less than 40 wt %, there are problems regarding the pour point, gelling temperature and bleeding, and, when the amount thereof is greater than 80 wt %, there is a problem in that the evaporation loss will be increased. Even when the amount of the tri-functional triester is greater than 20 wt %, there are problems in that the gelling temperature and hardness are excessively increased, and bleeding occurs. Further, when the amount of the di-functional triester is less than 20 wt % or greater than 60 wt %, the amount of the mono-functional triester and the tri-functional triester is relatively low or high compared to the amount of the di-functional triester, and thus the above-problems occur.

In the above Structural Formulae (1) to (9), the acyl group disposed at the ester end of the triester may have 6<21 carbon atoms, preferably, 6—13 carbon atoms. When the acyl group has less than six carbon atoms, the evaporation loss is increased, and, when the acyl group has greater than twenty one carbon atoms, the pour point of the plasticizer composition is not improved. In the present invention, it is considered that the benzoyl group relates to the characteristics of pour point, hardness and gelling temperature.

The plasticizer composition is prepared by the steps of: (a) fractional distillation of coconut oil methyl ester to obtain a fatty acid methyl ester of $C_6$~$C_{12}$; (b) mixing the fatty acid methyl ester with triacetin and methyl benzoate; and (c) transesterifying the mixture under a basic catalyst.

In the method of preparing the plasticizer composition according to the present invention, fatty acid methyl ester, which is a raw material, is obtained by the pretreatment of coconut oil methyl ester (biodiesel). Coconut biodiesel includes a methyl ester of $C_6$ to $C_{18}$ as a main component, and examples of the methyl ester may include methyl hexanoate, methyl octanoate, methyl decanoate, methyl dodecanoate (laurate), methy tetradecanoate(myristate), methyl hexadecanoate(palmitate), methyl octadecanoate (stearate), etc. In the present invention, the fatty acid methyl ester of $C_{6\sim C12}$ is separated by fractional distillation. Since the conditions and processes of fractional distillation are well known, the detailed description thereof will be omitted.

The separated fatty acid methyl ester of $C_6$~$C_{12}$ is mixed with triacetin and methyl benzoate at a predetermined molar ratio. In this case, based on the fatty acid methyl ester derived from coconut, the molar ratio of triacetin to fatty acid methyl ester may be 1~5, preferably, 1~3, and the molar ratio of methyl benzoate to fatty acid methyl ester may be 0.1~0.5, preferably, 0.1~0.3. When the molar ratio of triacetin to fatty acid methyl ester is less than 1, an excessive amount of di-functional triester and tri-functional triester are produced, and, when the molar ratio thereof is greater than 5, the amount of functional triesters does not fulfill the requiring composition of a plasticizer. Further, when the molar ratio of methyl benzoate to fatty acid methyl ester is less than 0.1, the amount of an acyl group of 6 to 21 carbon atoms is excessive, thus increasing the pour point of the plasticizer composition, and, when the molar ratio thereof is greater than 0.5, the amount of aromatic components is excessive, thus increasing the amount of a plasticizer decreased by volatilization.

In this method, the mixture of triacetin, fatty acid methyl ester and methyl benzoate may be pretreated (dewatered) under the conditions of reduced pressure and high temperature before transesterification. The pretreatment of the mixture may be performed at a pressure of 1~100 torr, preferably, 1~50 torr, and a temperature of 30~120° C., preferably 50~80° C.

The transesterification of the mixture is performed under a basic catalyst. The basic catalyst may be selected from sodium methoxide, sodium ethoxide, sodium propoxide, hydrotalcite, zeolite, potassium carbonate ($K_2CO_3$), potassium hydroxide (KOH), sodium hydroxide (NaOH), alkali earth metal oxides, alkali metal salt-supported alumina ($K_2CO_3/Al_2O_3$, $KOH/Al_2O_3$ or the like), lithium-enhanced calcium oxide (Li-enhanced CaO), etc.

Preferably, sodium methoxide or sodium ethoxide may be used as the basic catalyst, and the basic catalyst may be added to the plasticizer composition in an amount of 0.1~10 mol %, preferably, 1~6 mol % based on the total moles of triacetin. When the amount of the basic catalyst is less than 0.1 mol %, the yield of the plasticizer composition is low, and excessive expenses are required to maintain the conditions of a reactor. Further, when the amount thereof is greater than 10 mol %, side reactions rapidly proceed, and thus excessive expenses and time are required to additionally treat impurities. When the basic catalyst is a homogeneous catalyst, reaction products may be purified by adsorption and refined after removing unreacted products, impurities and the basic catalyst using work-up and distillation. When the basic catalyst is a heterogeneous catalyst, reaction products may be purified by adsorption and refined after removing unreacted products and impurities using distillation.

The transesterification reaction of the reaction mixture is performed for 2~6 hours. When the temperature of the reaction mixture is lower than 70° C. immediately after the addition of the basic catalyst, the reaction mixture is previously heated to a temperature of 70~120° C. in order to initiate the transesterification reaction. Particularly, the reaction mixture is heated to a target temperature at a heating rate of at least 1° C./min, preferably, at least 3° C./min, after the basic catalyst is added. However, in the case where the basic catalyst is a heterogeneous catalyst in which an alumina carrier is supported with an alkali metal oxide such as $K_2O$, $Li_2O$ or $Na_2O$, the transesterification reaction may be conducted at a temperature of 150~290° C. for 1~6 hours.

Further, after the transesterification reaction, a process of separating the methyl acetate produced by this transesterification reaction may be additionally conducted.

The triester-based plasticizer composition of the present invention may be suitably used for polyvinyl chloride resins, epoxy resins or urethane resins. Examples of the polyvinyl chloride resins may include chlorine-containing resins, such as chlorinated polyvinyl chloride, polyvinylidene chloride, chlorinated polyethylene, vinyl chloride-vinyl acetate copolymer, vinyl chloride-propylene copolymer, vinyl chloride-styrene copolymer, vinyl chloride-isobutylene copolymer, vinyl chloride-vinylidene chloride copolymer, vinyl chloride-vinyl ether copolymer, and blends thereof, and synthetic resin containing no chlorine, such as acrylontrile-styrene copolymer, acrylonitrile-styrene-butadiene terpolymer, ethylene-vinyl acetate copolymer, polyester, and blends thereof, block copolymers and graft copolymers thereof.

Further, the present invention provides a resin composition, comprising the plasticizer composition in an amount of 10~100 phr based on polyvinyl chloride resin, epoxy resin or urethane resin. Methods of preparing the resin composition using the plasticizer composition are not particularly limited, and are well known in the related field.

MODE FOR INVENTION

Hereinafter, the present invention will be described in more detail with reference to the following Examples. However, these Examples are set forth to illustrate the present invention, and the scope of the present invention is not limited thereto. In these Examples, the physical properties of samples were evaluated by the following method.

Hardness

Based on the ASTM D2240, the needle of a hardness tester (A type) was completely pressed onto one point of a sample for 5 seconds, and then the hardness of the sample was measured. Hardness tests were conducted at three points of each sample, and then the average value thereof was obtained. Hardness is used as an index for representing plasticizing efficiency.

Tensile strength, elongation, elastic modulus at 100% elongation The tensile strength and elastic modulus of a sample were measured using UTM based on the ASTM D412 method. The tensile strength and elastic modulus thereof were measured at the cut point of a dumbbell-shaped sample after it was pulled at a crosshead speed of 200 mm/min. The elastic modulus at 100% elongation corresponds to the tensile strength at 100% elongation, and is deeply related to plasticizing efficiency.

Pour point

Based on ASTM D97 method, the pour point of a sample is designated as the temperature at which the sample does not move for 5 seconds when it is inclined by a pour point tester.

Gelling Temperature

The gelling temperature is designated as the temperature at which a maximum of G'(storage modulus) is observed by heating the sample using a rheometer.

EXAMPLE 1

1.3 mol of triacetin, 1 mol of coconut oil-based fatty acid methyl ester (methyl octanoate) and 0.3 mol of methyl benzoate (MB) were put into a 2L round flask provided with a stirrer and a condenser, and were then dewatered at a reduced pressure of 5 torr and a temperature of 70° C. Subsequently, 5 mol % (based on triacetin) of sodium methoxide was added, and then the mixture was heated to 110° C. while stirred, to conduct a reaction for 3 hours.

Methyl acetate side-produced during the reaction was removed by conducting depressurization to 50 torr at 100° C. using a vacuum pump. Meanwhile, the reaction product was neutralized by a 10% HCl aqueous solution, and was then phase-separated into an organic layer and a water layer. The organic layer was water-washed, dewatered and then filtered using an adsorbent to obtain an ester-based plasticizer composition. The components of the obtained plasticizer composition were observed using gas chromatography (GC). The molar ratios of the reactants and the composition ratios of the product are given in Table 1 below.

EXAMPLES 2 to 4

Plasticizer compositions were prepared in the same manner as Example 1, except that the mixing ratios of triacetin, coconut oil-based fatty acid methyl ester and methyl benzoate were changed. The molar ratios of the reactants and the composition ratios of the products are given in Table 1 below.

COMPARATIVE EXAMPLES 1 TO 6

Comparative Examples 1 and 2 relate to commonly-used plasticizers DOP(di-octyl-phthalate) (Comparative Example 1) and DINP(Di-iso-nonylphthalate) (Comparative Example 2). Comparative Examples 3 to 5 relate to plasticizer compositions prepared in the same manner as Example 1, except that the mixing ratios of triacetin, coconut oil-based fatty acid methyl ester of 13 to 18 carbon atoms and methyl benzoate were changed. The molar ratios of the reactants and the composition ratios of the products are given in Table 1 below. Meanwhile, Comparative Example 6 relates to a plasticizer composition including 15 wt % of glyceryl tri-octanoate, 35 wt % of glyceryl bis-(octanoate)mono-benzoate, 35 wt % of glyceryl bis-(benzoate)mono-octanoate and 15 wt % of glyceryl tri-benzoate.

TABLE 1

|  | Molar ratios of reactants | | | | Composition ratios of products (wt %) | | | |
| --- | --- | --- | --- | --- | --- | --- | --- | --- |
|  | Triacetin | FAME Light | FAME | Methyl benzoate | Mono- | Di- | Tri- | Ratios of aromatic components in products |
| Ex. 1 | 1.3 | 1 |  | 0.3 | 43 | 40 | 17 | 22 |
| Ex. 2 | 1.5 | 1 |  | 0.3 | 52 | 38 | 10 | 24 |
| Ex. 3 | 2 | 1 |  | 0.3 | 61 | 32 | 7 | 23 |
| Ex. 4 | 3 | 1 |  | 0.3 | 71 | 24 | 5 | 22 |
| Comp. Ex. 1 | 6 |  | 1 | 0 |  |  |  |  |
| Comp. Ex. 2 | 1 |  | 0.4 | 0.1 |  |  |  |  |
| Comp. Ex. 3 | 1 |  | 0.5 | 0.3 |  |  |  |  |

TEST EXAMPLE

Test samples were fabricated in order to evaluate the performance of the ester-based plasticizer compositions obtained in the Examples and Comparative Examples. That is, 50 phr of the prepared plasticizer composition and 1 phr of a stabilizer (LFX-1100) were mixed with polyvinyl chloride resin (LS-100, manufactured by LG Chemicals Co., Ltd.), and then the mixture was preheated to 185° C. for 1 minute, pressurized for 1.5 minutes and cooled for 2 minutes to obtain a sheet having a thickness of 2 mm. The sheet was formed into various test dumbbell-shaped samples, and the following tests were conducted using these test samples.

TABLE 2

|  | Pour point | Bleeding | Hardness | Tensile strength | Elongation | Gelling temperature |
| --- | --- | --- | --- | --- | --- | --- |
| Ex. 1 | −23 | no | 78.7 | 185 | 334 | 131 |
| Ex. 1 | −25 | no | 80.2 | 198 | 329 | 129 |
| Ex. 1 | −27.5 | no | 78.4 | 199 | 326 | 127 |
| Ex. 1 | −25 | no | 77.9 | 194 | 329 | 126 |
| Comp. Ex. 1 | <−40 | no | 80.8 | 183 | 321 | 129 |
| Comp. Ex. 2 | <−40 | no | 84.6 | 192 | 298 | 137 |
| Comp. Ex. 3 | −8 | no | 80.6 | 181 | 337 | 139 |
| Comp. Ex. 4 | −8 | slight | 81.0 | 190 | 315 | — |
| Comp. Ex. 5 | −8 | slight | 83.3 | 201 | 310 | — |
| Comp. Ex. 6 | <−40 | slight | 83.0 | 213 | 299 | 130 |

As given in Table 2, it is presumed that the plasticizing efficiency of the test examples of the present invention is similar to that of a conventional phthalate plasticizer because the hardness of the test examples of the present invention is similar to that of DOP, and that the test examples fabricated using the plasticizer composition of the present invention can be put to various practical uses because they have higher tensile strength than that of DOP and have elongation similar to that of DOP. Further, it is determined that the tensile strength or elongation of the test examples fabricated using the plasticizers of Comparative Examples 3 to 5 is not greatly improved considering that the tensile strength or elongation of the test examples thereof is lower than that of the test example fabricated using the conventional phthalate plasticizer. Further, it can be seen that the hardness and pour point of the test examples fabricated using the plasticizers of Comparative Examples 3 to 5 is not greatly improved because the hardness thereof is higher than that of DOP and the pour point thereof is much higher than that of DOP and DINP. Moreover, it can be seen that the test example fabricated using the plasticizer of Comparative Example 6 has poor miscibility and thus has insufficient compatibility because it has a low pour point and high hardness and because the bleeding phenomenon whereby a plasticizer is discharged therefrom occurs.

From the results of Tables 1 and 2, it can be seen that the plasticizer compositions of Examples 1 to 4 have a plasticizing efficiency equal to or higher than that of DOP or DINP which is the most commonly-used plasticizer. Since the novel plasticizer composition of the present invention has high plasticizing efficiency, it can be variously formed depending on its use, and thus it is expected that it can be variously used.

As described above, although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing a plasticizer composition, comprising:
   fractionating coconut oil methyl ester to obtain a fatty acid methyl ester of C6 to C12;
   mixing the fatty acid methyl ester with triacetin and methyl benzoate; and
   transesterifying the mixture using a basic catalyst,
   wherein the produced plasticizer composition includes glycerin triester having, based on the total amount of the plasticizer composition,
       40-80 wt % mono-functional triester,
       20-60 wt % di-functional triester, and
       0-20 wt % tri-functional trimester;
   wherein the plasticizer composition comprises 15-40 wt % aromatic components;
   and
   wherein
       the mono-functional triester is a structure in which one benzoyl group or one acyl group of 6 to 21 carbon atoms is disposed at the ester end thereof, the other ester end groups are acetyl groups, the di-functional triester is a structure in which two benzoyl groups or two acyl groups of 6 to 21 carbon atoms is disposed at the ester end thereof, the other ester end groups are acetyl groups, and the tri-functional triester is a structure in which three benzoyl groups or three acyl groups of 6 to 21 carbon atoms is disposed at the ester end thereof.

2. The method according to claim 1, wherein the fatty acid methyl ester has a carbon number of 6 to 12.

3. The method according to claim 1, wherein, in the mixing the fatty acid methyl ester with triacetin and methyl benzoate, a mixing molar ratio of fatty acid methyl ester: triacetin: methyl benzoate is 1:1 to 5:0.1 to 0.5.

4. The method according to claim 3, wherein the mixing molar ratio of fatty acid methyl ester: triacetin: methyl benzoate is 1:1 to 3:0.1 to 0.3.

5. The method according to claim 1, further comprising: removing moisture from the mixture at a pressure of 1 to 100 torr and a temperature of 30 to 120° C. before transesterifying the mixture.

6. The method according to claim 1, wherein the basic catalyst is sodium methoxide or sodium ethoxide.

7. The method according to claim 1, wherein the basic catalyst is added in an amount of 0.1 to 10 mol % based on the total amount of triacetin.

8. The method according to claim 1, wherein transesterifying the mixture is conducted at a temperature of 70 to 120° C.

9. The method according to 1, wherein transesterifying the mixture is conducted at a temperature of 150 to 290° C. under a heterogeneous catalyst in which an alumina carrier is supported with alkali metal oxide.

10. The method according to claim 9, wherein the alkali metal oxide is $K_2O$, $Li_2O$ or $Na_2O$.

11. A plasticizer composition comprising:
   glycerin triester having, based on the total amount of the plasticizer composition,
      40-80 wt % mono-functional triester,
      20-60 wt % di-functional triester and
      5-20 wt % tri-functional triester;
   wherein
      the plasticizer composition comprise 15-40 wt % aromatic components;
      the mono-functional triester is a structure in which one benzoyl group or one acyl group of 6 to 21 carbon atoms is disposed at one ester end thereof and the other ester end groups are acetyl groups,
      the di-functional triester is a structure in which two benzoyl groups or two acyl groups of 6 to 21 carbon atoms is disposed at two ester ends thereof and the other ester end group is an acetyl group, and
      the tri-functional triester is a structure in which three benzoyl groups or three acyl groups of 6 to 21 carbon atoms is disposed at the three ester ends thereof.

12. A resin composition, comprising the plasticizer composition of claim 11 in an amount of 10-100 phr based on a polyvinyl chloride resin, an epoxy resin, or a urethane resin.

* * * * *